(12) United States Patent
Wölfel et al.

(10) Patent No.: US 10,639,491 B2
(45) Date of Patent: May 5, 2020

(54) POSITIONING AID FOR TRANSCRANIAL MAGNETIC STIMULATION

(71) Applicant: MAG & More GmbH, München (DE)

(72) Inventors: Markus Wölfel, München (DE);
Christian Hirschbeck, München (DE);
Kerstin Häringer, München (DE)

(73) Assignee: MAG & More GmbH, München (DE)

( * ) Notice: Subject to any disclaimer, the term of this patent is extended or adjusted under 35 U.S.C. 154(b) by 275 days.

(21) Appl. No.: 15/906,006

(22) Filed: Feb. 27, 2018

(65) Prior Publication Data

US 2018/0250521 A1  Sep. 6, 2018

(30) Foreign Application Priority Data

Mar. 6, 2017  (DE) .......................... 10 2017 104 627

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01)

(58) Field of Classification Search
CPC ................................................ A61N 2/00–12
See application file for complete search history.

(56) References Cited

U.S. PATENT DOCUMENTS

| 6,926,660 | B2 | 8/2005 | Miller |
| 7,651,459 | B2 | 1/2010 | Cameron et al. |
| 8,088,058 | B2 | 1/2012 | Juliana et al. |
| 2006/0287566 | A1* | 12/2006 | Zangen ..................... A61N 2/02 600/15 |
| 2010/0113959 | A1 | 5/2010 | Pascual-Leone et al. |
| 2015/0202453 | A1 | 7/2015 | Topp et al. |
| 2016/0015588 | A1* | 1/2016 | Tamiya ..................... A61N 2/00 128/845 |
| 2016/0030762 | A1 | 2/2016 | Glass et al. |
| 2017/0291037 | A1* | 10/2017 | Tamiya ..................... A61N 2/00 |

FOREIGN PATENT DOCUMENTS

| DE | 10242542 | A1 * | 4/2004 | ............ A61N 2/006 |
| DE | 10242542 | A1 | 4/2004 | |
| DE | 102008034237 | A1 | 2/2010 | |
| EP | 2252367 | B1 | 9/2015 | |
| EP | 2878336 | A1 | 6/2016 | |
| WO | 03098268 | A1 | 11/2003 | |
| WO | 2008130533 | A2 | 10/2008 | |
| WO | 2016056326 | A1 | 4/2016 | |

* cited by examiner

*Primary Examiner* — Catherine B Kuhlman
(74) *Attorney, Agent, or Firm* — Coats + Bennett, PLLC (57) ABSTRACT

The device for positioning a magnetic coil for transcranial magnetic stimulation in relation to the head of a patient includes a head unit with a support for the patient's head and a positioning unit, which is connected to the support, with a coil seat for holding the magnetic coil. The device also includes a fixedly installed holding arm holding the head unit. A reversibly movable connection is provided between the head unit and the holding arm, and configured such that a change of a force, which is applied onto the support by the head of the patient, leads to a relative movement between the head unit and the holding arm through the movable connection.

20 Claims, 5 Drawing Sheets

POSITIONING AID FOR TRANSCRANIAL MAGNETIC STIMULATION

This application claims the benefit under 35 USC § 119 of German application DE 102017104627.5, filed 6 Mar. 2017, the disclosure of which is incorporated herein by reference in its entirety.

FIELD OF THE INVENTION

The present invention relates to a device for positioning a magnetic coil in relation to the head of a patient, as well as a method for positioning a magnetic coil in relation to the head of a patient.

BACKGROUND

Transcranial magnetic stimulation (TMS) is a non-invasive method for stimulating or inhibiting of neuronal networks in the brain. Besides brain research, it is also used for therapeutic treatment for example of depression.

The correct and reproducible positioning of a magnetic coil used in this process on the head of the patient is one of the most important requirements of TMS. Individual stimulation points, so-called hot spots, have to be identified for each patient and have to be found once again for each session. The stimulation coil has to be positioned at the desired stimulation point and remain continuously in this position during a session. To relieve the neck of the patient during the sessions, either a vacuum cushion for relaxed positioning of the head or a patient armchair with an integrated headrest is used.

In everyday clinical practice, hats or bathing caps, on which the individual stimulation points of a patient are marked, are mostly used. To determine a suitable stimulation point and a suitable stimulation intensity, the head is measured and possible stimulation points (a so-called 9-point grid) are marked. Then, the brain area that represents the hand function in the brain is sought based on the marked grid through emission of stimulation pulses with sufficient intensity and an appropriate orientation of the coil. During stimulation of the right place with sufficient intensity, the reaction of the thumb is measured. The point with the best reaction is marked on the cap. The individual stimulation intensity is measured here, and this point serves in addition as a starting point for measuring and marking of the individual therapy point (e.g. by means of the 5 cm rule). This individually measured therapy point is marked on the cap and used as a place of stimulation for each session. The positioning of the coil has to be ensured during treatment through holding of the coil or through clamping into a holding device. Fixation and/or support of the head is not taken into account in this process and can be ensured separately, e.g. through a vacuum cushion or an appropriate neckrest on the patient armchair. This method is very easy to learn and a cost-efficient solution. However, the stimulation points cannot be found once again with a 100% accuracy because the cap cannot be put on in exactly the same way for a second time. In addition, the head of the patient must not move during stimulation and the coil has to be held in a way that it will not change the position on the head for the period of stimulation.

Further, the use of coil positioning systems in which the coil is positioned in relation to the head on the basis of holding and measurement tools is known. In these systems, the patient must not change the position of the head during stimulation because the coil positioning systems cannot follow the movement of the head and/or the contact of the coil to the head is measured by means of a sensor and because stimulation is stopped when the coil loses con-tact with the head (e.g. due to a head movement). In addition, a special patient armchair, which supports the head of the patient during stimulation, has to be used when this method is applied.

Neuro-navigation systems can be used for high-precision positioning of the coil. Said systems use MRT photographs of the respective patient in order to create a three-dimensional model of the head and the brain. By means of ultrasound or infrared tracking systems, the positions of the coil and the head/brain in relation to one another are determined in real time and displayed in the 3D model. With this, the coil can be positioned very easily over the area to be stimulated and the position of the coil can be saved. Although finding of the right stimulation point through neuro-navigation is not necessarily facilitated (the therapy point has to be measured manually as in case of using the caps), this method offers very good reproducibility and a documentation possibility of the stimulation point as soon as said stimulation point is determined thanks to diverse memory possibilities of the coil-head coordinates. However, also in this method both the coil, which is held manually or by means of a holding system, as well as the head of the patient have to be held steady during the entire stimulation period as the stimulation position will otherwise be left. In addition, the costs for purchasing such a sys-tem are very high. Furthermore, the user has to be trained on the use of computers, software and navigation systems.

A relatively new development is a TMS robot as a type of intelligent coil holder that holds the coil automatically in the position marked in the navigation in relation to the head of the patient by means of a neuro-navigation system and that guides it along in case of a movement of the patient. The TMS robot can move the coil in three or more directions and therefore can ensure in connection with a sensor the respective positioning and the contact of the coil to the head. The large space, technology and training requirement to operate the expensive robot is disadvantageous.

A positioning system for navigated transcranial magnetic stimulation is known from DE 102 42 542 A1. The positioning system comprises a support bar as a holder for a bracket on which a second bracket is fastened via two rotary suspension devices and in a way that it can be swiveled around a swivel axis. A trolley is disposed on the second bracket in a motor-driven way. The stimulation coil is fastened on the trolley by means of a motor-driven adjustment possibility. By means of motor-driven swiveling of the second bracket around the swivel axis, motor-driven movement of the trolley along the second bracket and motor-driven adjustment of the adjustment possibility on the trolley, the position of the stimulation coil can be adjusted in relation to the head of a patient. In addition, a support for the head of the patient is fastened on the support bar. To keep the head of the patient in a fixed place, the support has fastening elements in form of a belt that is strapped around the forehead of the patient and presses the head of said patient onto the support in a way as to fix it. Alternatively, supports with additional form- and/or force-fitting clamping devices or clampings for the patient's head should be provided. By installing the support as a fixation of the patient's head on the support bar, patient movements should be reduced. The support bar can for example be installed on a seat for the patient. Neither the support for the head nor the fixation elements for fixing the head on the support should limit the patient's field of vision. The treatment can still be unpleasant for the patient because his head must not and cannot be moved during adjustment of the position of the stimulation coil as well as during the entire treatment. In particular in case of repeated treatment, this can lead to tensions in the neck area and/or to headaches.

Further positioning systems for transcranial magnetic stimulation are known from U.S. Pat. Nos. 6,926,660; 7,651,459; 8,088,058; and U.S. Patent Application publications 2010/0113959, 2015/0202453, and 2016/0030762; and from European patent EP2252367.

SUMMARY

The present disclosure provides a device for positioning of a magnetic coil in relation to the head of the patient, as well as a respective positioning method, that advantageously cause no or only very little discomfort for the patient even in case of a longer holding time of the magnetic coil.

According to the invention, a device for positioning of a magnetic coil for transcranial magnetic stimulation in relation to the head of a patient is provided. The device comprises a head unit with a support for the head of the patient and with a positioning unit that is connected to the support. The positioning unit comprises a coil seat for holding the magnetic coil. In addition, the device comprises a holding arm that can be installed in a firm way and that holds the head unit.

The holding arm can for example be fastened on or at least in relation to a floor or a wall of the treatment room or a patient armchair in a fixed way. It is also possible to install the holding arm on an equipment cart. Installable in a fixed way should mean in relation to the holding arm that its position and orientation after the installation is determined at least to the extent that it will not be moved or shifted by typical movements of the head of the patient that impact on it via the support. Preferably, the holding arm can be selectively set to an adjustment mode and to an installed mode. In the adjustment mode, the holding arm can be adjusted to the suitable positioning with regard to the patient by means of one or multiple adjustment possibilities. For example a height adjustment through partial elements of the holding arm that are plugged into one another in a telescopic way in order to adapt the holding arm to a height of the patient. Alternatively or in addition, multiple partial segments of the holding arm can be tiltable in the adjustment mode in relation to one another. From the adjustment mode, the holding arm can for example be set to the installed mode through locking of the partial elements, which are plugged into one another in a telescopic way, in relation to one another and/or through locking of the swivel connections of its partial segments so that the holding arm is installed in a fixed way.

According to the invention, a movable connection is provided between the head unit and the holding arm. The movable connection is formed in such a way that a change of the force applied to the support by the head of the patient leads to a relative movement between the head unit and the holding arm through the movable connection. The connection between the head unit and the holding arm is reversibly movable. This means that a relative movement between the head unit and the holding arm that is caused by a change of the force, which is applied to the support by the head of the patient, can be reversed (in contrast for example to a ratchet-like movability). It is clear that within the meaning of the invention the relative movement between the head unit and the holding arm should occur in a non-destructive way.

The support held by the holding arm bears at least a part of the weight of the head and there-fore enables a comfortable and relaxed positioning of the head, also during a longer period of time. As the head unit is held by the holding arm, the entire weight of the head unit as well as of a magnetic coil fastened on said head unit does not have to be carried by the head of the patient. This aspect is also advantageous for a relaxed positioning of the head. The system is preferably self-carrying.

Due to a movable connection between the head unit and the holding arm, the head unit can react to a change of the head position of the patient or a change of a pressing or application force of the head onto the support with a relative movement in relation to the holding arm. Hence, a firm fixation of the head is no longer necessary and the patient always has the possibility to leave the device by himself. This leads, among other aspects, to the device being perceived as particularly reassuring by the patient. In addition, the emergency procedure in case of an epileptic seizure of the patient or similar incidents is simplified.

The movable connection between the head unit and the holding element is formed preferably as a permanently movable connection. This can mean that the movable connection is un-lockable and/or does not have any locking position. This ensures that the position of the head unit adapts to the force that is applied onto the support by the head of the patient regardless of the current operating status.

The positioning unit can be connected to the support in a rigid way or in a way that it can be fixed rigidly. Therefore, an optimal force transmission between the support and the rest of the head unit can be achieved. In particular, the force applied onto the support by the head of the patient is transmitted directly to the positioning unit with the installed coil. Particularly prefer-ably, the positioning unit can be displaced with regard to the support in an adjustment mode and can consequently be adapted to the head of the patient. After the adaptation, the relative position between the positioning unit and the support can be fixed with a fixation element so that there is a rigid connection between the positioning unit and the support.

The support is formed preferably in a way that a change of the force, which is applied onto the support by the head of the patient and/or a movement of the head that is supported by the support, leads to the head unit being guided along with a movement of the head. For example, turning the head to the left or to the right can lead to such a change of the force, which is applied onto the support by the head, that the head unit also turns to the left or to the right through the movable connection, i.e. that it follows the head. In this process, the relative position between the magnetic coil held by the coil seat and the head of the patient can remain at least essentially constant. Due to the head unit being guided along, an amount of the position shift between the head and the magnetic coil can be attenuated during movement of the head. Therefore, the patient can move his head to a certain extent without the need to adjust the position of the magnetic coil once again.

Preferably, the position of the coil seat remains the same in relation to the support during the relative movement between the head unit and the holding arm through the movable connection. This ensures that the magnetic coil that is held in the coil seat will not change its position in relation to the head supported by the support at least in essential terms.

According to a preferred embodiment, the movable connection between the head unit and the holding arm can counteract the force applied onto the support by the head of the patient in an elastic way. Through the elastic counterforce, the head of the patient receives an optimal support that is adapted to the head position and the respective contact force of the head. If an increased force is applied onto the support by the head of the patient, said force can move against the spring effect in relation to the holding arm. Due to this, a restoring force into the preceding position can arise so that the head unit is moved into the preceding position by the restoring force in case of a new reduction of the force applied to the support by the head. In addition, a force pulse, which is applied abruptly onto the support by the head of the patient, is dampened so that no abrupt movements of the head unit will occur.

The movable connection between the head unit and the holding arm can comprise a translation coupling. The translation coupling can allow for a linear translation movement of the head unit in relation to the holding arm with respect to a translation direction that is at least essentially parallel to the viewing direction of a head supported by the support, i.e. in a front-rear direction of the head. Hence, the patient can adapt his sitting position for example by shifting his head, which is supported by the support, to the front or to the back.

The translation coupling can have one or two end stops that delimit the movement range of the translation coupling. A first end stop can prevent detachment of the head unit from the holding arm. A second end stop can limit a movement of the support to the rear.

The translation coupling can comprise a spring device. The spring device can be formed to be tensioned in case of an increase of a component, which is parallel to the translation direction of the translation coupling, of the force applied onto the support by the head of the patient and a resulting linear translation movement of the head unit along the translation direction. In case of a subsequent reduction of the component, which is parallel to the translation direction, of the force applied onto the support by the head, the spring device can impinge the head unit to an opposed linear translation movement due to the tension. Hence, if the patient presses his head for example against the support to the rear, the support can move to the rear against the viewing direction of the head (movement in relation to the support arm) and the spring unit will be tensioned. If the pressing force to the rear changes later due to a position change of the head or a changed body tension of the patient, or if the patient moves his head to the front, the support will be guided along to the front due to the tension of the spring unit. The spring unit can be for example a helical spring or a pneumatic or hydraulic spring device. A spring constant of the spring device can be chosen as needed in order to support the patient's head as conveniently as possible.

In addition or as an alternative to the translation coupling, the movable connection between the head unit and the holding arm can comprise one or multiple rotary couplings that allow for a swivel movement of the head unit in relation to the holding arm. The movable connection preferably comprises a first rotary coupling that allows for a swivel movement of the head unit about a first axis and/or a second rotary coupling that allows for a swivel movement of the head unit about a second axis and/or a third rotary coupling that allows for a swivel movement of the head unit about a third axis. By providing multiple, in particular three, rotary couplings, the head unit can follow movements of the head supported by the support relatively freely. Preferably, the first, the second and the third axis are at least essentially positioned at a right angle to one another so that there will be a particularly large movement range of the movable connection between the holding arm and the head unit.

For example, the first axis can extend at least essentially in parallel to a dorso-caudal axis (top-bottom direction) in relation to a head supported by the support. Thus, due to the first rotary coupling, the head unit can follow a movement of the head that corresponds to a view to the left or right (like in case of shaking one's head).

The second axis can extend at least essentially in parallel to an ear-ear axis (lateral direction) in relation to a head supported by the support. Thus, due to the second rotary coupling, the head unit can follow a movement of the head that corresponds to an upward or downward inclination (like in case of nodding).

The third axis can extend at least essentially in parallel to a torso-rostral axis (nose-back of the head or front-rear direction) with regard to a head supported by the support. Thus, due to the third rotary coupling, the head unit can follow a movement of the head that corresponds to tilting of the head towards a shoulder.

Also in relation to the rotary coupling(s), providing respectively one or multiple end stop(s) is conceivable.

Preferably, the positioning unit comprises at least one positioning element that is adjustable in relation to the support for adjusting the position of the coil seat. Due to this, the coil held by the coil seat can be brought into a suitable position with regard to the head of the patient. The adjustment of the positioning element is preferably independent of the relative movement between the head unit and the holding arm through the movable connection. In particular, the setting of the positioning element can be lockable.

Particularly preferably, the positioning unit comprises a tiltable first positioning element, in particular in form of a bracket, and a second positioning element that is installed movably on said first positioning element and on which the coil seat is installed in a fixed or adjustable way. The first positioning element and the second positioning element provide two degrees of freedom of setting the coil position.

To be able to reuse a setting of the coil position for subsequent sessions, at least one scale can be provided on which a swiveling position of the first positioning element (e.g. angular dimension indication) and/or a displacing position of the second positioning element (e.g. longitudinal dimension indication) can be read. The values read from the at least one scale allow for simple and accurate recovery of the coil position for another session.

The support preferably comprises a neckrest that can, in particular, be padded.

In addition, the support can comprise a side support, respectively, on both sides of the neckrest. The side supports can each be installed tiltably on the neckrest, in particular with hinges, in a way that they can be placed laterally with respect to a head of a patient that is supported by the neckrest and that they are lockable in relation to the neckrest in a placement position. Through the supports, the relative position between the head and the head unit can be held particularly well. In addition, a very good force transmission between the head and the support is achieved so that an automated guiding of the head unit during movements of the head is facilitated.

Preferably, the head unit can be brought into a defined position with regard to the head of the patient at the start of the adjustment. For this purpose, for example features of the cranial bone (inion, nasion and/or tragi) an/or of the head can be used. For at least two, preferably three of such points, a searcher can be provided on the head unit. If the head unit is oriented in relation to at least two features of the cranial bone and/or of the head, an unambiguous positioning of the of the head unit in relation to the head will be provided. This can ensure that the head unit will be positioned identically with regard to the patient's head for successive sessions.

Searchers for features of the cranial bone and/or of the head can be formed for example as openings in the positioning unit. By means of one or multiple openings in the positioning units as ear position searchers, for example distinctive ear positions (e.g. tragus) can be targeted. In addition or alternatively, such ear position searchers can comprise a source for a light beam, e.g. a LED, by means of which the searched ear position can be targeted.

Alternatively or in addition, the support, in particular the neckrest, can comprise a sensorial opening as a inion searcher for localizing the inion of a head that is supported by the support. The sensorial opening offers sufficient space for a finger of a user and can be aligned with the inion on the back of the patient's head.

In addition, the invention relates to a method for positioning a magnetic coil in relation to the head of a patient. The device according to the invention for positioning a magnetic coil in relation to the head of a patient is suitable for implementing the method according to the invention. Features and explanations described in relation to the device can also be transferred to the method and vice versa.

A method according to the invention for positioning a magnetic coil in relation to the head of a patient comprises providing a firmly (in particular in relation to a treatment room) installed holding arm. A head unit is installed on the holding arm in such a way that the holding arm holds the head unit. The head unit comprises a support for the head of the patient and a positioning unit, which is connected to the support, with a coil seat for holding the magnetic coil. The head unit is installed on the holding arm in such a way that it can be moved reversibly in such a way that a change of a force, which is applied to the support by the patient's head, leads to a relative movement between the head unit and the holding arm through the movable connection between the head unit and the holding arm. For adjusting the coil seat in relation to the support, the positioning unit is adjusted to a desired treatment position for the magnetic coil.

As already described with regard to the device, the support installed on the holding arm sup-ports the head of the patient in its position. Due to the movable installation of the head unit on the holding arm, moving of the patient's head supported by the support is possible without losing the set position of the magnetic coil in relation to the head. Firm fixation of the head of the patient is no longer required.

Evidently, the patient's convenience during positioning of the magnetic coil and during holding of said coil in said position in relation to the head is significantly improved by the invention. In addition, incorrect application and/or a premature stop of an application through movement of the head in relation to the magnetic coil is prevented to a great extent. This improvement of patient convenience and application implementation and the specific technical realization of positioning and holding of the magnetic coil in relation to the patient's head, and not a treatment of the patient by means of electromagnetic fields generated by the magnetic coil, should be the core of the invention. In particular, therapy methods can be excluded from the invention.

In case of a change of the force applied onto the support by the head of the patient, the head unit can be guided automatically along with a movement of the patient's head due to the movable connection between the head unit and the holding arm. In this automatic guiding of the head unit, in particular the setting of the positioning unit can be maintained and hence the position of the coil elements in relation to the support can remain the same.

As already described with regard to the device, the method can comprise elastic counteracting against the force applied to the support by the head of the patient due to the movable connection between the head unit and the holding arm. In particular, the movable connection can have the translation coupling described above for this purpose.

DESCRIPTION

The Figures show an embodiment of a device 1 according to the invention for positioning a magnetic coil 2 in relation to the head of a patient. The magnetic coil 2 can be suitable for performing a transcranial magnetic stimulation.

Figure 1:
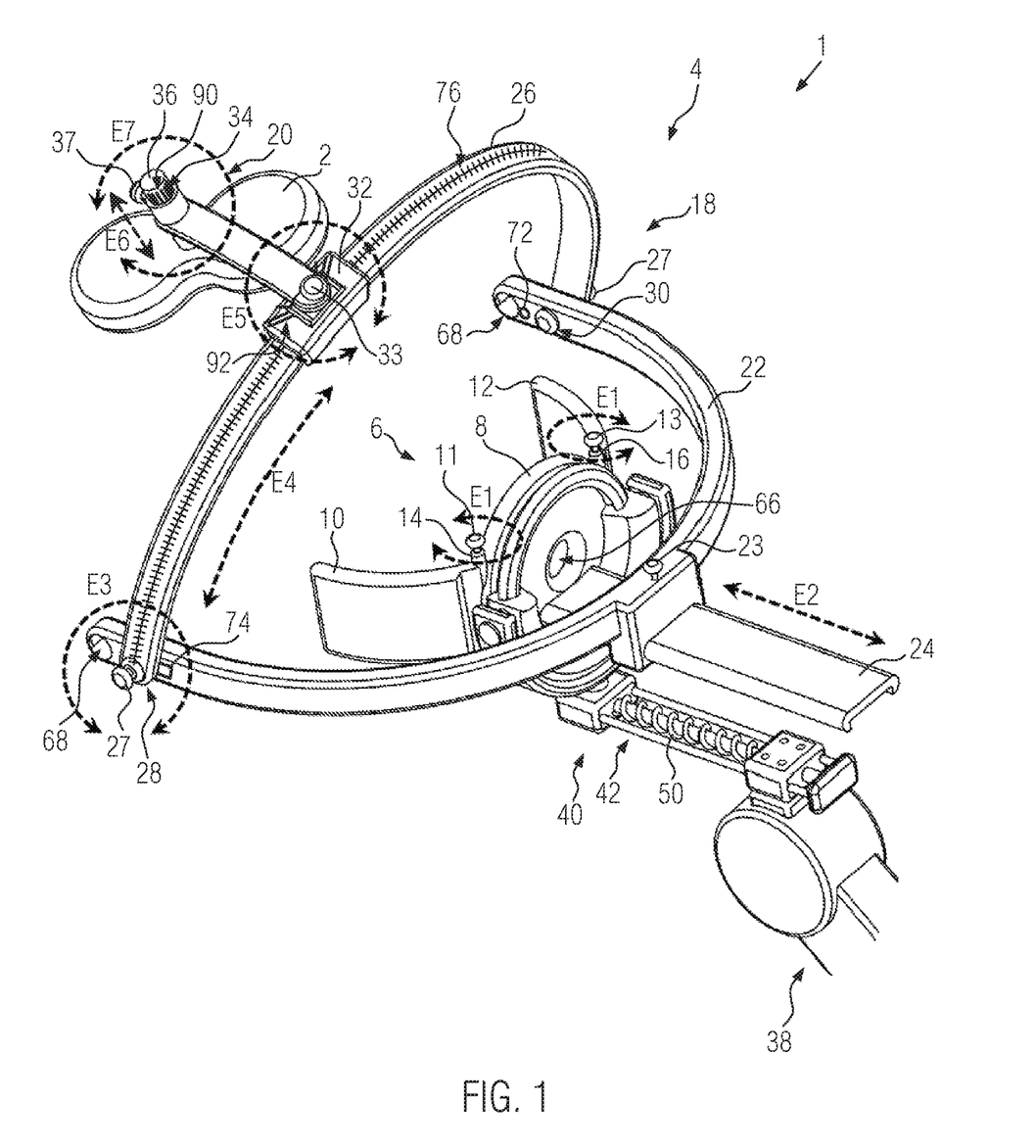
FIG. 1 shows a schematic perspective partial view of a device for positioning a magnetic coil in relation to the head of a patient according to an embodiment, in particular for illustrating diverse adjustment possibilities of the head unit.

As can be seen for example in the part of the device 1 displayed in FIG. 1, the device 1 comprises a head unit 4 with a support 6 for the head of the patient. The support 6 comprises a neckrest 8 against which the patient's head can be leaned. In addition, the support 6 comprises respectively one side support 10, 12 on both sides of the neckrest 8 in relation to an ear-ear axis (lateral direction) of a head supported by the support 6. The side supports 10, 12 are installed on the neckrest 8 in a tiltable way and respectively via a hinge 14, 16. The tiltability of the side supports 10, 12 is illustrated by the respective arrows E1 in FIG. 1. After the patient has leaned the back of his head against the neckrest 8, the side supports 10, 12 can be fitted laterally to the patient's head by means of the hinges 14, 16. In the fitted position, the side supports 10, 12 can be fixed in relation to the neckrest 8, for example by means of screws 11, 13 or other fixation elements.

Furthermore, the head unit 4 has a positioning unit 18, which is connected to the support 6, with a coil seat 20 for holding the magnetic coil 2. The positioning unit 18 comprises a base bracket 22 by means of which the positioning unit 18 is connected to the support 6. For this purpose, the support 6 comprises a backward-extending rail 24 on the side of the neckrest 8 that faces away from the head of the patient. On this rail 24, the base bracket 22 of the positioning unit 18 is installed in a way that it can be displaced in parallel to a front-rear direction (viewing direction) of a head supported by the support 6. A corresponding movability is illustrated by the arrow E2 in FIG. 1. Through displacement of the base bracket 22 along the rail 24, the position of the positioning unit 18 can be adapted to the head size of the patient in a personalized way as described in greater detail further below. If the desired setting position of the positioning unit 18 in relation to the support 6 is achieved, the base bracket 22 can be fixed in its position on the rail 24 by means of a screw or another suitable fixation element.

For setting a desired position of the magnetic coil 2 in relation to the head of the patient sup-ported by the support 6, the positioning unit 18 further comprises a first positioning element 26 in form of a bracket that is installed on the base bracket 22 on both of its ends in a way as to be tiltable about an axis that is essentially parallel to the ear-ear axis (lateral direction). A respective tilting movement is illustrated by the arrow E3 in FIG. 1. The corresponding swivel connections 28, 30 between the base bracket 22 and the first positioning element 26 are synchronized via the first positioning element 26. After being set into a suitable tilting position, the first positioning element 26 can be fixed in its current tilting position in relation to the base bracket 22 by means of a suitable fixing element such as a screw 27. It can be sufficient if one of the two swivel connections 28, 30 can be fixed. However, separate fixing elements can also be provided for both swivel connections 28, 30.

Furthermore, the positioning unit 18 comprises a second positioning element 32 that is movably installed on the first positioning element 26 along the first positioning element 26. The movability of the second positioning element 32 is illustrated by the arrow E4 in FIG. 1. The second positioning element 32 can be fixed in its position on the first positioning element 26 by means of a suitable fixing, for example a screw 33. The second positioning element 32 carries the coil seat 20 for the magnetic coil 2.

In the illustrated embodiment, the coil seat 20 is installed adjustably on the second positioning element 32. In particular, the coil seat 20 in the embodiment can be rotated about an axis that is at least essentially perpendicular to the shifting direction E4 of the second positioning element 32 with respect to the second positioning element 32 (rotation direction E5). This rotation of the coil seat 20 can also be locked via the fixing element for the second positioning unit 32, i.e. via the screw 33. It would also be conceivable to install the coil seat 20 firmly on the second positioning element 32. In both cases, the coil seat 20 can be brought into a desired position in relation to the head supported by the support 6 by means of swiveling the first positioning element 26 in relation to the base bracket 22 (arrow E3) and/or shifting of the second positioning element 32 along the first positioning element 26 (arrow E4).

In the shown embodiment, the coil seat 20 comprises an opening 34 for receiving a bolt 36 that is fastened on the magnetic coil 2. By means of a sliding movement of the bolt 36 in the opening 24, the magnetic coil can be moved towards the head surface from above or away from said head surface in order to optimize the distance between the magnetic coil 2 and the head (arrow E6). In addition, the bolt 36 can be rotated around its extension axis in order to also adjust, where required, a rotary orientation of the magnetic coil 2 about an axis that is essentially perpendicular to the head surface (arrow E7). After approaching the head surface with the magnetic coil 2, possibly up to contact, and a suitable rotary adjustment around the extending direction of the bolt 36, the magnetic coil 2 can be adjusted to its position in relation to the coil seat 20 through fixing the bolt 36 in the opening 34 of the coil seat 20 by means of a suitable fixing element such as a screw 37.

Figure 2:
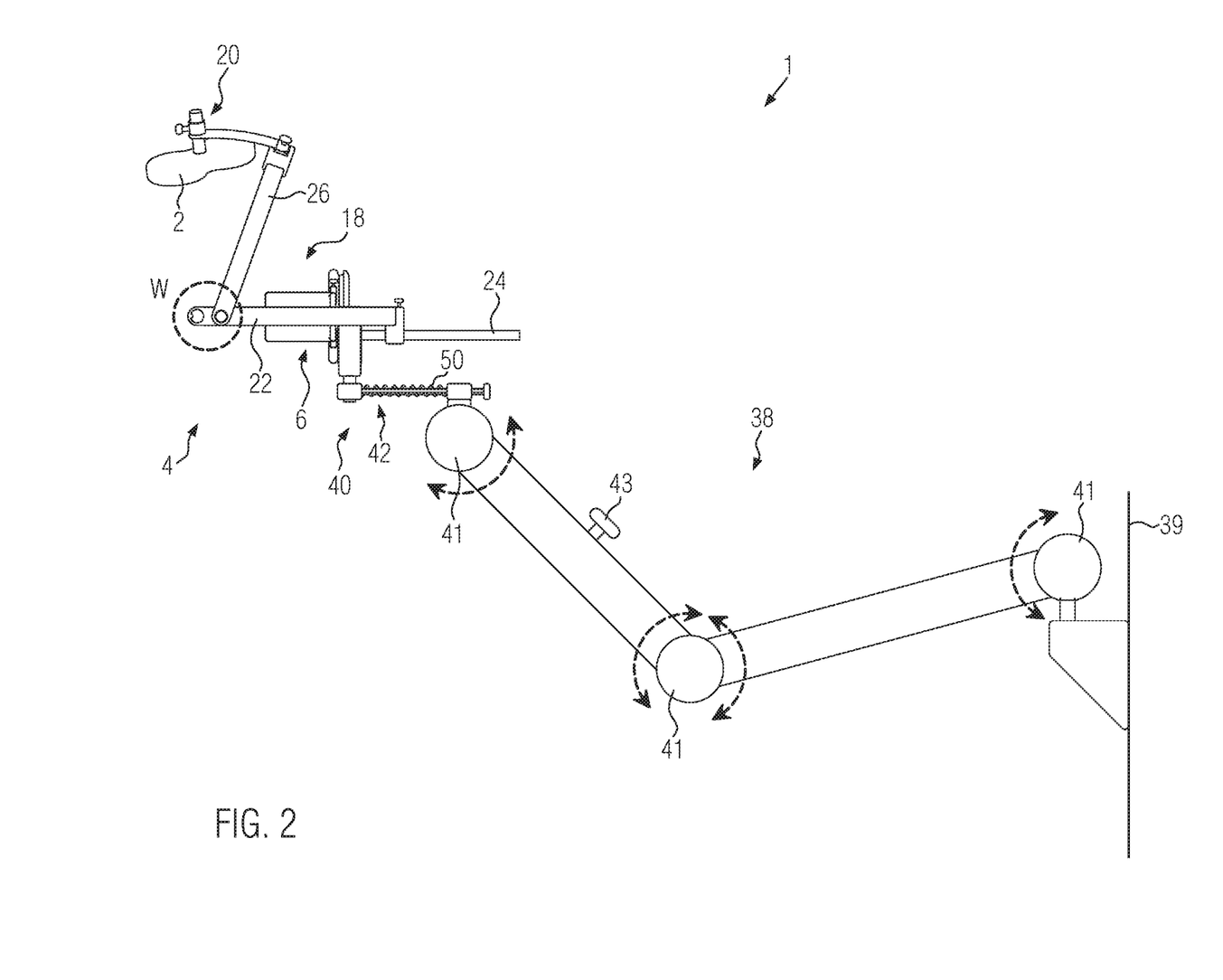
FIG. 2 shows a schematic side view of the device according to the embodiment.

The device 1 for positioning the magnetic coil 2 in relation to the head of the patient further comprises a holding arm 38 that can be installed firmly and that holds the head unit 4 and that is shown only partially in FIG. 1. The side view according to FIG. 2 provides a good overview over the device 1 according to the embodiment and shows the complete holding arm 38. As shown there, the holding arm 38 is installed firmly on a wall in the illustrated variant. It is for example also conceivable to install the holding arm 38 firmly on a floor of a treatment room, on an equipment cart, or on a patient armchair, or at least in relation to said devices. Firmly installable should mean in relation to the holding arm 38 that its position and orientation is fixed after the installation at least to the extent that it will not be moved or shifted by typical movements of the patient's head that impact on it through the support 6 and the head unit 4.

The illustrated holding arm 38 can selectively be set to a setting mode and to an installed mode. In the setting mode, the holding arm 38 can be moved to the suitable positioning with regard to the patient by means of agile shifting possibilities 41 provided between partial segments of the holding arm 38. From the setting mode, the holding arm 38 can be brought to the installed mode through locking of the agile shifting possibilities 41 by means of a joint actuating element 43 so that the holding arm 38 is installed in a firm way.

Figure 3:
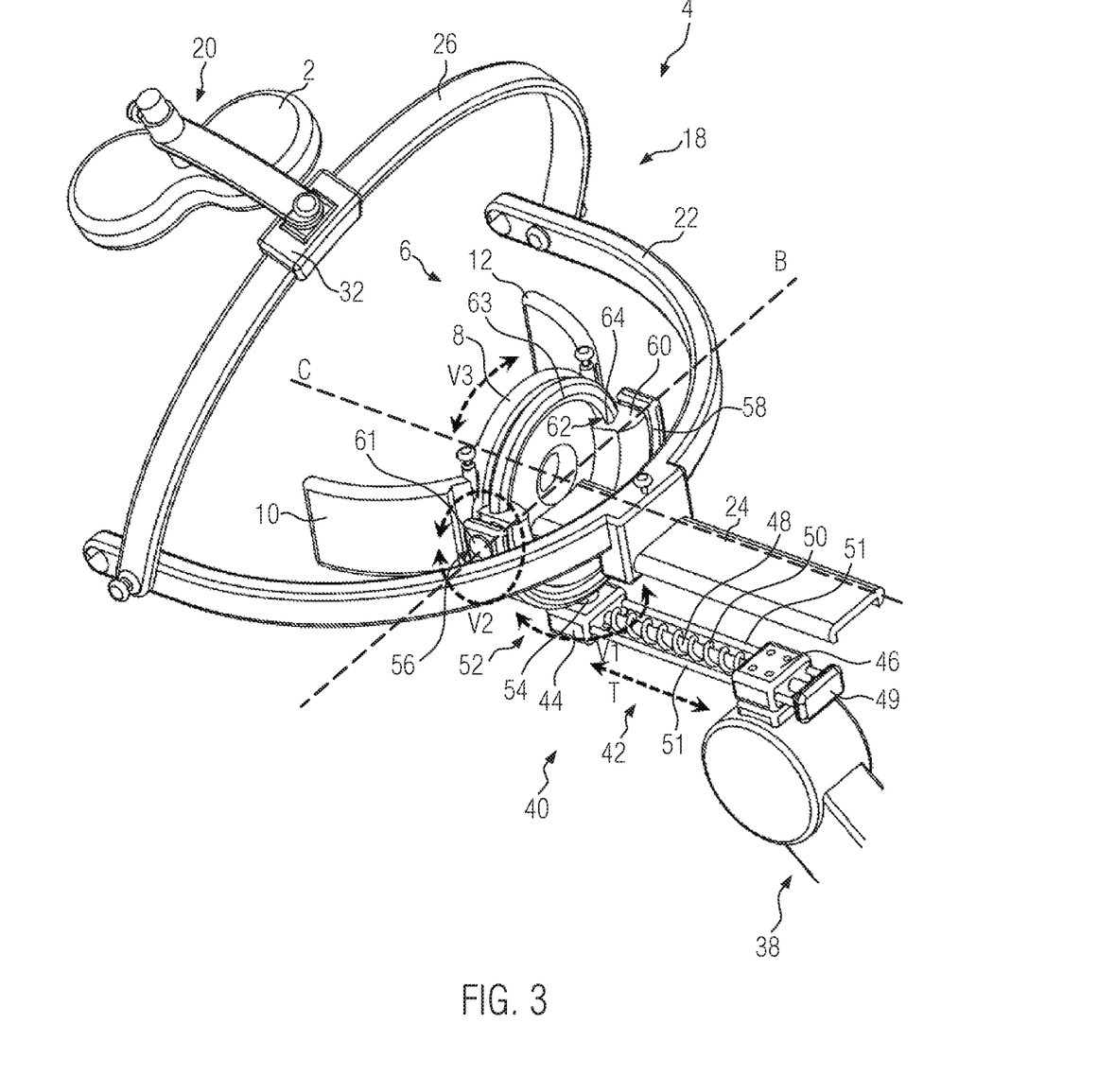
FIG. 3 shows a schematic perspective partial view according to the embodiment, which corresponds to the view from FIG. 1, in particular for illustrating the movable connection between the holding arm and the head unit.

A reversibly movable connection 40 is provided between the head unit 4 and the holding arm 38. Said connection is at least partially visible in FIGS. 1 and 2. For the sake of clarity, however, reference is made primarily to FIGS. 3 and 4 for the description of the movable connection 40. Apart from the displayed reference signs and movement arrows, FIG. 3 is identical to FIG. 1. In the shown embodiment, the movable connection 40 comprises a translation coupling 42 (see in particular FIG. 3) between the head unit 4 and the holding arm 38, which allows for a linear translation movement of the head unit 4 in relation to the holding arm 38 with respect to a translation direction T that is essentially parallel to the viewing direction of a head supported by the support 6. The translation coupling 42 comprises a coupling element 44 on the side of the head unit 4 on which the head unit 4 is installed as well as a coupling element 46 on the side of the holding arm 38 that is installed on the holding arm 38, in particularly installed in a firm way. A bolt 48, which penetrates the coupling element 46 on the side of the holding arm 38 in a sliding way in relation to the translation direction T, is fixed to the coupling element 44 on the side of the head unit 4. Due to the sliding installation of the bolt 48 in the coupling element 46 on the side of the holding arm 38, the coupling element 44 on the side of the head unit 4 with the head unit 4 installed on it can be moved towards the holding arm 38 or away from it in relation to the translation direction T. In the direction towards the holding arm 38, engagement of the coupling element 44 on the side of the head unit 4 with the coupling element 46 on the side of the holding arm 38 can provide an end stop that limits the movement. A movement of the coupling element 44 on the side of the head unit 4 away from the holding arm 38 is limited by an end stop that is formed as a bulge 49 on the bolt 48 for engagement with the coupling element 46 on the side of the holding arm 38. For stabilization of the translation coupling 42, guiding bars 51 are fastened on the coupling element 44 on the side of the head unit 4 on both sides and in parallel to the bolt 48 and guided in a sliding way in the coupling element 46 on the side of the holding arm 38 in relation to the translation direction T in the illustrated embodiment.

A spring device 50 in form of a helical spring is provided between the coupling elements 44, 46 of the translation coupling 42. When the coupling element 44 on the side of the head unit 4 is moved towards the holding arm 38, the spring device 50 is tensioned so that a restoring force arises that impinges the coupling element 44 on the side of the head unit 4 away from the holding arm 38 with respect to the translation direction T. If a patient leans his head against the support 6, the head unit 4 is moved towards the holding arm 38 via the translation coupling 42 and against the spring device 50 with respect to the translation direction T due to the support force of the head onto the support 6, in particular onto the neckrest 8. At a certain point, the support force applied by the head onto the support 6 and the restoring force of the spring 50 are balanced so that a stationary state is reached in which the head rests on the support 6. If the support force of the head onto the support 6 is reduced or increased, for example due to a movement of the head, the translation coupling 42 will adapt automatically.

Figure 4A:
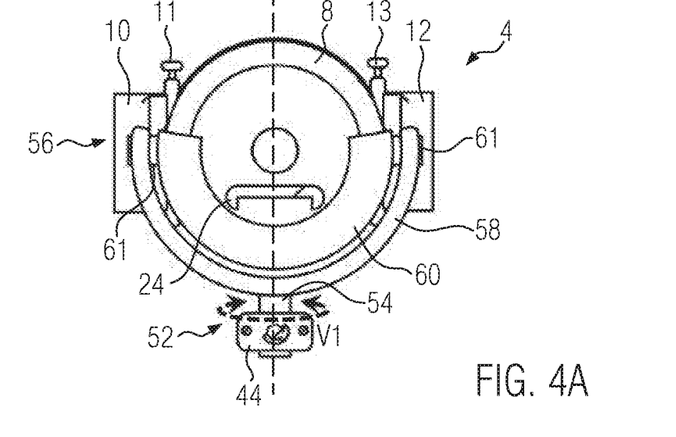
FIG. 4A shows a schematic partial rear view onto the device according to the embodiment.
Figure 4B:
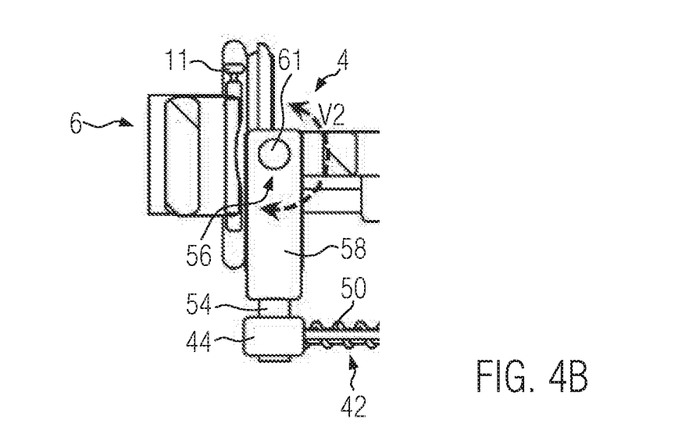
FIG. 4B shows a schematic partial side view onto the device according to the embodiment.
Figure 4C:
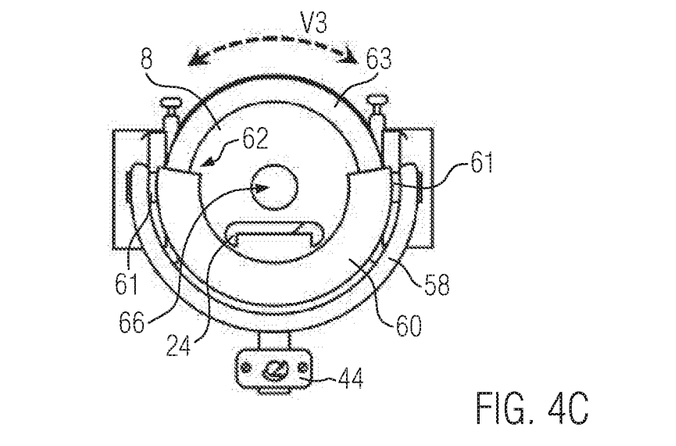
FIG. 4C shows a further schematic partial rear view onto the device according to the embodiment.

The movable connection 40 between the head unit 4 and the holding arm 38 further comprises a first rotary coupling 52. The first rotary coupling 52 can be seen particularly well in the partial rear view in FIG. 4A besides FIG. 3. The first rotary coupling 52 allows for a swivel movement of the head unit 4 about a first axis A that extends at least essentially in parallel to a dorso-caudal axis (top-bottom direction) in relation to a head supported by the support 6. A respective swivel movement of the head unit 4 is illustrated in FIGS. 3 and 4A by the arrow V1. In the shown embodiment, the first rotary coupling 52 is implemented in that a bolt 54 that is fastened on the coupling element 44 on the side of the head unit 4 of the translation coupling 42 is installed on the head unit 4 in a way as to be rotatable around the first axis A. It would also be conceivable to install the bolt 54 firmly on the head unit 4 and rotatably on the coupling element 44 on the side of the head unit 4. The first rotary coupling 52 enables the head unit 4 to follow a movement of the head with respect to the fixed holding arm 38 that corresponds to a rotation of the head to the left or right (just as in case of shaking one's head). If the patient turns his head supported by the support 6 to the left or right, the head unit 4 will be induced to follow the movement of the head through a contact with the side supports 10, 12 of the support 6.

The movable connection 40 between the head unit 4 and the holding arm 38 comprises in addition a second rotary coupling 56. The second rotary coupling 56 can be seen particularly well in the sectional side view onto the device 1 in FIG. 4B besides FIG. 3. The second rotary coupling 56 allows for a swivel movement of the head unit 4 in relation to the fixed holding arm 38 about a second axis B that extends at least essentially in parallel to an ear-ear axis (lateral direction) in relation to a head supported by the support (perpendicular to the drawing plane in FIG. 4B). In the shown embodiment, the second rotary coupling 56 is implemented in that a frame element 58, which is installed on the bolt 54 of the first rotary coupling 52, is connected on two points, which are spaced from one another along the second axis B respectively with a rotary bolt 61, to a holding element 60 (see also FIGS. 4A and 4C) that is connected to the head unit 4 in a way that it can be swiveled around the second axis B. Due to the second rotary coupling 56, the head unit 4 can follow a movement of the head, which corresponds to an upward or downward inclination (as in case of nodding) in relation to the fixed holding arm 38. A corresponding rotary movement of the head unit 4 is illustrated by the arrow V2 in FIGS. 3 and 4B. If the patient performs a respective head movement, the support force of the head onto the support 6, in particular onto its neckrest 8, will change. This force change is transformed into a corresponding movement of the head unit 4 in relation to the stationary holding arm 38 by the second rotary coupling 56.

The movable connection 40 between the head unit 4 and the holding arm 38 further comprises a third rotary coupling 62. Besides in FIG. 3, the third rotary coupling 62 can be seen particularly well in the partial rear view in FIG. 4C that corresponds to FIG. 4A apart from the displayed reference signs and direction arrows. The third rotary coupling 62 allows for a swivel movement of the head unit 4 around a third axis C that extends at least essentially in parallel to a dorso-rostral axis (nose-back of the head or front-rear direction) in relation to a head supported by the support 6. In the shown embodiment, the third rotary coupling 62 is implemented in a way that a flange 63 that circulates on the back of the neckrest 8 is absorbed along a part of its circumference in a complementary, semicircular groove 64 of the holding element 60. The flange 63 of the neckrest 8 is absorbed in the groove 64 of the holding element 60 in a sliding way so that the neckrest 8 is installed in the holding element 60 for a rotary movement around the third axis C. This way, the head unit 4 can follow the movement of the head, which corresponds to tilting of the head to a shoulder of the patient (both in the direction towards the left as well as in the direction towards the right shoulder) due to the third rotary coupling 62. A respective rotary movement of the head unit 4 is displayed by the arrow V3 in FIGS. 3 and 4C. If the patient performs a respective head movement, a resulting change of the support force onto the support 6, in particular via the side supports 10, 12 of the support, is transformed into a corresponding movement of the head unit 4.

The translation coupling 42 as well as the first, second and third rotary coupling 52, 56, 62 are formed as permanently movable connections and cannot be locked.

In the following, the adjustment of the position of the magnetic coil 2 in relation to the head of a patient will be explained.

At the beginning of the adjustment, at first the head unit 4 should be brought into a defined position in relation to the patient's head that can be reproduced for subsequent sessions. For this purpose, the head unit 4 is aligned based on features of the cranial bone and/or the head of the patient. After the patient has leaned his head against the neckrest 8 of the support 6 (possibly already before in a rough setting), a general position of the head unit 4 is set by means of the adjustment possibilities 41 of the holding arm 38. According to the displayed embodiment, this can occur by means of a inion searcher provided on the neckrest 8 for localizing the inion on the back of the patient's head. The inion searcher is formed as a sensorial opening 66 (see FIG. 1) through the neckrest 8. This sensorial opening 66 can be centered on the back of the patient's head in relation to the inion. Besides setting a suitable height for the head unit 4, the head unit 4 is also centered on the patient's head in this process. The adjustment possibilities 41 of the holding arm 38 can be locked after the finished adjustment and the holding arm 38 can therefore be set to its firmly installed state.

Figure 5:
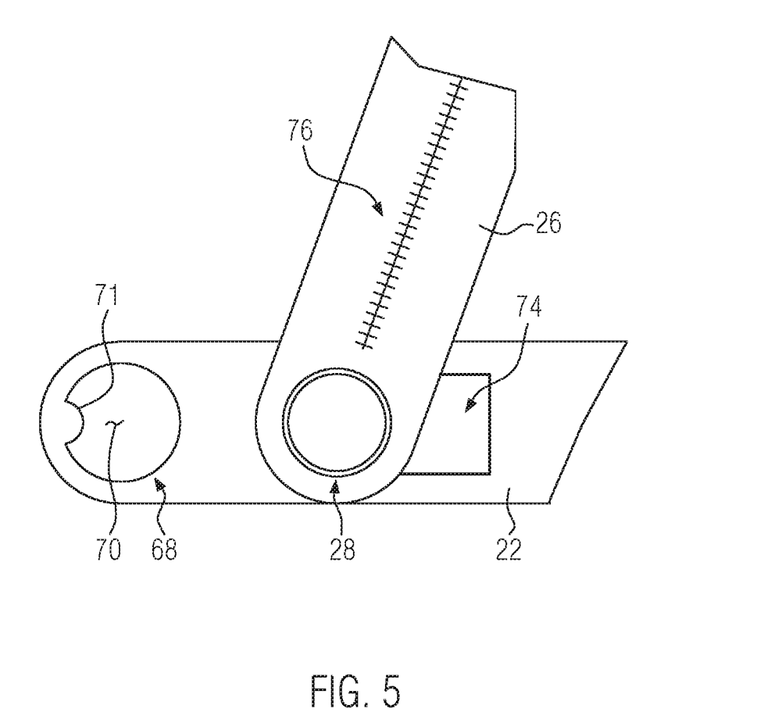
FIG. 5 shows a schematic detail view of part W from FIG. 2.

After the neckrest 8 has been aligned on the inion, the head unit 4 can in addition be oriented on ear features (e.g. the tragi) of the head. For this purpose, the positioning unit 18 comprises respectively one ear position searcher 68 on both ends of its base bracket. In the displayed embodiment, the ear position searchers 68 respectively comprise an opening 70 in the base bracket 22 through which respective points of the ear such as the tragi can be targeted. The opening 70 can comprise a target element such as a protrusion 71 in order to enable an even more accurate targeting of respective points of the ear. The ear position searchers 68 can be seen for example in FIGS. 1 and 3. One of the ear position searchers 68 is shown in detail in FIG. 5 that is an enlarged illustration of the section W from FIG. 2. In addition or as an alternative, the ear position searchers 68 can each comprise a source 72 for a light beam such as a LED in order to target the ear features with the light beam. To align the positioning unit 18 with the ear features, the positioning unit 18 is shifted on the rail 24 that is installed firmly on the support 6 until the ear position searchers 68 are located directly above the respective points of the ears. Then, the base bracket 22 of the positioning unit 18 is fixed on the rail 24. If the ear position searchers 68 are located above or below the targeted points of the ear, this can be corrected through detachment of the holding arm 38, appropriate tilting of the head unit 4 and a subsequent new fixation of the holding arm 38. Subsequently, the two side supports 10, 12 can be guided laterally towards the head via the swivel connections 14, 16 and fixed there. Therefore, the head is held in position in relation to the head unit 4 in order to enable a good force transmission between the head and the head unit 4.

As soon as the head unit 4 is oriented as a whole in relation to the head, the coil seat 20 can be set to the desired relative position to the head of the patient by means of deflection of the first positioning element 26 (arrow E3) and shifting of the second positioning element 32 along the bracket-shaped first positioning element 26 (arrow E 4). Where required, the magnetic coil 2 can still be adapted in the coil holder 20 in its distance to the head surface (arrow E6) and/or in its rotary orientation (arrow E7). Also an adaptation of the position of the coil seat 20 in relation to the second positioning element 32 according to arrow E5 is conceivable. Subsequently, the swivel position of the bracket-shaped first positioning element 26 in relation to the base bracket 22 as well as the shifting position of the second positioning element 32 in relation to the bracket-shaped first positioning element 26 and the position of the magnetic coil 2 in relation to the coil seat 20 as well as the position of the coil seat 20 with regard to the second positioning element 32 are fixed with the respective fixing elements.

To simplify the adjustment procedure for subsequent sessions, scales 74, 76 are provided on which the swivel position of the first positioning element 26 and the shifting position of the second positioning element 32 can be read. A first scale 74 (FIG. 5) enables reading of the swivel position of the first positioning element 26 in relation to the base bracket 22. A second scale 76 enables reading of the shifting position of the second positioning element 32 along the first positioning element 26. For the sake of clarity, the scales are only displayed schematically in FIGS. 1 and 5. The first scale can be provided as an angular scale on the base bracket 22 and the second scale 76 can be provided as a longitudinal scale along the first positioning element 26. The scales 74, 76 can be read as soon as a suitable position of the magnetic coil 2 has been found. For reading and later readjustment of a swivel position of the coil seat 20 in relation to the second positioning element 32 and of a rotary orientation of the magnetic coil 2 around bolts 36, scales 90, 92 are conceivable on the coil seat 20 and the bolt 36. In a subsequent session, the swivel position of the first positioning element 26 as well as the shifting position of the second positioning element 32 can be set based on the recorded or saved scale values and no new experimental determination of the optimal treatment point has to take place. Also a reproduction of the swivel position of the coil seat 20 in relation to the second positioning element 32 and/or reproduction of the angular orientation of the magnetic coil 2 in relation to the coil seat are possible based on the respective scale values.

While the sliding connection of the base bracket 22 on the rail 24 (arrow E2), the swivel connection 28, 30 of the first positioning element 26 with the base bracket 22 (arrow E3), the shifting connection of the second positioning element 32 with the first positioning element 26 (arrow E4), the swivel connection of the coil seat 20 with the second positioning element 32 (arrow E5) and the rotary connection of the magnetic coil 20 with the coil seat 20 (arrow E7) are fixed after their adjustment, the movable connection 40 (translation coupling 42 and first, second and third rotary coupling 52, 56, 62) is constantly movable (arrows V1, V2 and V2), in particular also during treatment of the patient. As described above, the movable connection 40 with its individual couplings allows the head unit 4 to be moved along with movements of the head. In the resulting movements of the head unit 4 in relation to the holding arm 38, the position of the coil seat 20 in relation to the support 6 and hence the relative position of the coil 2 in relation to the head remains at least essentially constant as the shifting connection between the positioning unit 18 and the rail 24 has been locked.

The displayed embodiments are only exemplary and the complete scope of the present invention is defined by the claims.

What is claimed is:

1. A device for positioning a magnetic coil for transcranial magnetic stimulation in relation to the head of a patient, the device comprising:
   a head unit comprising:
      a support for the head of the patient configured to bear at least part of the weight of the head; and
      a positioning unit connected to the support, the positioning unit having a coil seat for holding a magnetic coil; and
   a holding arm that holds the head unit and that can be installed firmly;
   a reversibly movable connection between the head unit and the holding arm, the movable connection configured such that a change of a force, which is applied onto the support by the head of the patient, results in a relative movement between the head unit and the holding arm through the movable connection.

2. The device of claim 1, wherein the movable connection is formed as a permanently movable connection.

3. The device of claim 1, wherein the positioning unit is connected to the support in a way that the positioning unit can be fixed rigidly.

4. The device of claim 1, wherein the support is configured such that the change of the force, which is applied onto the support by the head of the patient, results in the head unit being guided along with a movement of the patient's head.

5. The device of claim 1, wherein the head unit is configured such that a position of the coil seat in relation to the support remains the same during relative movement between the head unit and the holding arm.

6. The device of claim 1, wherein the movable connection is configured to elastically counteract the force applied onto the support by the patient's head.

7. The device of claim 1, wherein the movable connection comprises a translation coupling that allows for a linear translation movement of the head unit, in relation to the holding arm, in a translation direction that is generally parallel to a viewing direction of a head supported by the support.

8. The device of claim 7, wherein the translation coupling comprises a spring device that is configured to:

be loaded in response to an increase of a component of the force applied onto the support by the patient's head that is parallel to the translation direction and a resultant linear translation movement of the head unit in the translation direction; and act upon the head unit, in response to a subsequent reduction of the force component, to urge the head unit to move opposite the translation direction.

9. The device of claim 1:
wherein the movable connection comprises:
  a first rotary coupling that allows for a swivel movement of the head unit about a first axis; and/or
  a second rotary coupling that allows for a swivel movement of the head unit about a second axis; and/or
  a third rotary coupling that allows for a swivel movement of the head unit about a third axis,
wherein the first axis, the second axis, and the third axis are each positioned generally orthogonal to one another.

10. The device of claim 1, wherein the positioning unit comprises at least one positioning element that can be adjusted for adjusting the position of the coil seat in relation to the support.

11. The device of claim 1, wherein the positioning unit comprises a tiltable first positioning element and a second positioning element that is installed on the first positioning element in a shiftable way; wherein the coil seat is installed on the second positioning element.

12. The device of claim 11, further comprising at least one scale from which a swivel position of the first positioning element and/or a shifting position of the second positioning element can be read.

13. The device of claim 1, wherein the support comprises a cushioned neckrest.

14. The device of claim 13:
wherein the support comprises a respective side support disposed on each lateral side of the neckrest;
wherein the side supports are moveably mounted to the neckrest in such a way that:
  the side supports can be fitted laterally to a patient's head that is supported by the neckrest; and
  the side supports can be locked in a placement position in relation to the neckrest.

15. The device of claim 13, wherein the neckrest comprises a sensorial opening as an inion searcher.

16. The device of claim 1: wherein one or multiple ear position searchers are provided on the positioning unit by means of which distinctive ear positions can be targeted; and wherein the ear position searchers comprise an opening in the positioning unit and/or a source for a light beam.

17. A method for positioning of a magnetic coil in relation to the head of a patient, the method comprising:
providing a firmly installed holding arm;
installing a head unit on the holding arm so that the holding arm holds the head unit; the head unit comprising:
  a support for the head of the patient configured to bear at least part of the weight of the head; and
  a positioning unit connected to the support, the positioning unit comprising a coil seat for holding the magnetic coil;
adjusting the positioning unit to adjust the position of the coil seat in relation to the support to a desired treatment position for the magnetic coil;
wherein the head unit is installed on the holding arm in a reversibly movable way by a movable connection such that a change of a force, which is applied onto the support by the patient's head, results in a relative movement between the head unit and the holding arm through the movable connection.

18. The method of claim 17, further comprising automatically guiding the head unit to move along with a movement of the patient's head in response to a change of the force, which is applied onto the support by the patient's head, due to the movable connection between the head unit and the holding arm.

19. The method of claim 18, wherein, during the automatic guiding of the head unit, positioning of the positioning unit relative to the support is maintained and therefore positioning of the coil seat in relation to the support remains the same.

20. The method of claim 17, further comprising the movable connection elastically counteracting against the force, which is applied onto the support by the patient's head.

* * * * *